United States Patent [19]
Kopolow

[11] Patent Number: 5,711,951
[45] Date of Patent: Jan. 27, 1998

[54] AQUEOUS PRODUCT COMPRISING DISCRETE, STABILIZED, MICRODROPLETS OF AN OIL AND AN IN SITU POLYMERIZED VINYL MONOMER, CONTAINING A THICKENING AGENT TO HOMOGENEOUSLY SUSPEND THE MICRODROPLETS THROUGHOUT THE MEDIUM

[75] Inventor: Stephen L. Kopolow, Plainsboro, N.J.

[73] Assignee: ISP Investments Inc., Wilmington, Del.

[21] Appl. No.: 596,896

[22] Filed: Mar. 13, 1996

[51] Int. Cl.[6] .................... A61K 7/075; A61K 9/50; B01J 13/18
[52] U.S. Cl. .................... 424/401; 252/312; 264/4.7; 424/70.12; 428/402.22
[58] Field of Search .................... 252/315.1, 315.4; 264/4.7; 424/401, 497, 70.12; 428/402.22

[56] References Cited

U.S. PATENT DOCUMENTS

| | | | |
|---|---|---|---|
| 2,969,330 | 1/1961 | Brynko | 264/4.7 X |
| 3,436,452 | 4/1969 | Maierson | 428/402.22 X |
| 4,126,674 | 11/1978 | Mausner | 424/401 X |
| 4,155,741 | 5/1979 | Scher et al. | 424/497 X |
| 5,073,296 | 12/1991 | Kopolow et al. | 424/401 X |
| 5,084,208 | 1/1992 | Negrin et al. | 424/401 X |
| 5,252,325 | 10/1993 | Bires et al. | 424/401 X |

*Primary Examiner*—Richard D. Lovering
*Attorney, Agent, or Firm*—Marilyn J. Maue; Walter Katz; Joshua J. Ward

[57] ABSTRACT

An aqueous product includes discrete, stabilized, microdroplets of an oil and an in situ polymerized water-soluble vinyl monomer containing a thickening agent to suspend the microdroplets homogeneously throughout the medium.

14 Claims, No Drawings

AQUEOUS PRODUCT COMPRISING DISCRETE, STABILIZED, MICRODROPLETS OF AN OIL AND AN IN SITU POLYMERIZED VINYL MONOMER, CONTAINING A THICKENING AGENT TO HOMOGENEOUSLY SUSPEND THE MICRODROPLETS THROUGHOUT THE MEDIUM

BACKGROUND OF THE INVENTION

1. Field of the Invention

This invention relates to stabilization of an oil in water, and, more particularly, to a product including method for preparing stable, discrete, stabilized microdroplets having a high loading of an oil and an in situ polymerized water soluble vinyl monomer homogeneously suspended throughout the medium.

2. Description of the Prior Art

The unique properties of many oils make it desirable to include them in aqueous-based compositions. For example, cosmetically-active materials such as silicone oils, fluids and gums, mineral oils, and water-insoluble organic esters such as isopropyl palmitate and isopropyl myristate, are particularly useful in cosmetic formulations for the skin and hair. In such compositions, their lubricity properties impart conditioning action for the user. However, such oils are immiscible with water which makes it very difficult to maintain a stable aqueous dispersion without rapid separation of the composition into oil and water phases. To solve the problem of providing effective dispersibility of such materials in water, it has been necessary to include a surfactant in aqueous cosmetic compositions containing cosmetically-active oils in order to maintain dispersed droplets of the oil in the aqueous solution. However, the use of surfactants increases the cost of the product and even may affect the quality of the composition. In addition, even with a surfactant present, the stability of the dispersion is often not completely satisfactory.

Another approach is to form macroscopic capsules of an oil by in situ aqueous polymerization of oil soluble monomers. For example, Brynko, in U.S. Pat. Nos. 2,969,330 and 2,969,331, described the preparation of pressure-rupturable capsules of a chlorinated diphenyl oil in water by dissolving styrene, or an acrylate or vinyl acetate monomer, in the oil, dispersing the monomer-containing oil in water with the aid of an emulsifier to form droplets, and polymerizing the monomer to form an encapsulating wall of solid polymer material around each droplet of oil.

Berg, in J. Microencapsulation (1989) 6, No. 3, 327–337, also described a process for the microencapsulation of emulsified oil droplets by in situ vinyl polymerization. However, the process was limited to the use of methyl methacrylate, an oil soluble monomer, to form a polymer shell around emulsified oil droplets of decane and hexadecane.

De Luca, in U.S. Pat. No. 4,741,872, described the preparation of biodegradable microspheres having a three-dimensional network in which biologically active macromolecular agents were physically entrapped therein. The method involved emulsifying a vinyl derivative of a biodegradable hydrophilic polymer, a water-soluble monovinyl monomer, and a biologically active macromolecular agent, in water, and copolymerizing the vinyl compounds.

Kopolow, in U.S. Pat. No. 5,073,296, later described a method for preparing discrete microdroplets of an oil stabilized by in situ polymerization of a water-soluble vinyl monomer. The method comprised dispersing the oil in water, adding the water-soluble vinyl monomer, for example, vinyl pyrrolidone, and polymerizing the monomer in situ such that the oil was stabilized in the resulting polymer solution as discrete microdroplets. In order to effectively stabilize the microdroplets in the solution, without separating into two phases, it was necessary to provide a substantial amount of excess polymer therein to thicken the solution to maintain only a relatively low loading of oil. The presence of this excess amount of polymer in the solution, however, caused an undesirable increase in tack during use of the solution in cosmetic compositions.

Accordingly, it is an object of this invention to provide an aqueous product comprising discrete, stabilized microdroplets of a high loading of an oil and an in situ polymerized water-soluble vinyl monomer, containing an added thickening agent to maintain a predetermined viscosity for the solution, and to homogeneously suspend the microdroplets throughout the solution, at a high oil level therein.

Another object herein is to provide such a product without contributing to increased tack during use, and being stabilized for substantially an indefinite period of time.

Another object is to provide a method for making such discrete, stabilized microdroplets by in situ polymerization of a water soluble vinyl monomer, for example, vinylpyrrolidone, in the presence of dispersed droplets of a water-insoluble oil, for example, silicone oil, in water, and adding a thickening agent thereto, to maintain a predetermined viscosity in the product to homogeneously suspend the microdroplets throughout the medium.

Among the other objects of the invention is to provide a cosmetic formulation containing a product of discrete, stabilized microdroplets.

These and other objects and features of the invention will be made apparent from the following description thereof.

ABBREVIATIONS AND DEFINITIONS

Oil—A compound which is a water-insoluble liquid at room temperature and has an oily consistency VP—Vinylpyrrolidone MAPTAC—Methacrylamidopropyltrimethylammonium chloride PVP—Polyvinylpyrrolidone DM—Polydimethylsiloxane, such as Dimethicone, viscosity 100 cs, Petrarch Chem. Co; or 1000 cs, Dow Corning Corp.

MO—Mineral oil

TBP—Tert-butyl peroctoate, e.g. Trigonox® 21 (AKZO Chem. Co.),

TBPP—t-Butylperoxy pivalate, e.g. Lupersol® 11 (Atochem N. A.),

Cosmetically-active oil—An oil which imparts a particularly desirable property, e.g. lubricity, to a cosmetic formulation Brookfield viscosity—Bulk viscosity of stabilized oil-in-water product, in cps, as measured using an RVT spindle #5@20 rpm

SUMMARY OF THE INVENTION

What is provided herein is an aqueous product comprising discrete, stabilized microdroplets of an oil and an in situ polymerized water-soluble vinyl monomer containing an added thickening agent to suspend the stabilized microdroplets homogeneously throughout the composition.

A method for preparing such discrete, stabilized microdroplets also is described. The method comprises dispersing the oil in water to form microdroplets, adding a water-soluble vinyl monomer, such as vinylpyrrolidone, optionally with a comonomer polymerizable with the vinyl monomer, such as methacrylamidopropylammonium chloride, and polymerizing the monomer or comonomers, in situ, and then adding a thickening agent to provide a predetermined viscosity for the product, wherein the microdroplets are homogeneously suspended in the resultant solution.

In the preferred form of the invention, the oil is cosmetically-active, such as is characteristic of silicone oils, silicone gum blends, mineral oils and water-insoluble esters such as isopropyl myristate and isopropyl palmitate.

In a preferred form of the invention, with added thickening agent, a high loading of the oil in the microdroplet is achieved, while requiring only a relatively small amount of the polymer therein. In cosmetic application, such microdroplets enable the available oil to perform its cosmetic function without undesirable tack because of the presence of excess polymer in the solution.

DETAILED DESCRIPTION OF THE INVENTION

The active material to be dispersed in an aqueous medium are oils and gum blends which are water-insoluble liquids at room temperature, and preferably, are cosmetically-active, i.e. they impart a particularly desirable property to cosmetic formulations, for example, lubricity. Such cosmetically-active oils include silicone oils, silicone gum blends, mineral oils and water-insoluble esters such as isopropyl myristate and isopropyl palmitate.

Suitable silicone oils or fluids or gums for use in the invention may be selected from non-volatile polyalkyl siloxanes, polyaryl siloxanes, polyalkylaryl siloxanes and polyether siloxane copolymers. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL® series and from Dow Corning as the Dow Corning 200® products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cs, and most preferably, a viscosity of up to about 15,000 cs.

Suitable non-volatile polyalkylarylsiloxanes include, for example, polymethylphenylsiloxanes having viscosities of about 15 to 65 cs at 25° C. These siloxanes are available, for example, from General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to about 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Blends of silicone gums or high viscosity dimethicone fluids with low viscosity dimethicone fluids also may be used.

Other suitable oils for use herein include cosmetically-active materials such as light and heavy mineral oils, and water-insoluble organic esters such as isopropyl palmitate and isopropyl myristate.

In the practice of the present invention, the oil to be dispersed is first added to water and then subjected to agitation to produce a fine dispersion of discrete oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer such as vinylpyrrolidone itself, or a derivative thereof, such as an alkyl vinyl pyrrolidone, is added to the mixture, along with an appropriate free radical polymerization initiator. If desired, a comonomer is added for purposes of forming a copolymer. Suitable comonomers include dimethylaminopropyl methacrylate, dimethylaminoethyl methacrylate, methacrylamidopropyltrimethylammonium chloride, acrylamide and neutralized acrylic acid.

Suitable free radical polymerization initiators for polymerization of water-soluble vinyl monomers include free radical catalysts such as t-butylperoctoate, t-butylperoxypivalate and the like. Oil-soluble catalysts are preferred.

Then the reaction mixture is maintained at a temperature in the range of about 55° to 85° C., preferably, about 75° to 85° C., and most preferably, about 78° to 82° C., for a period of time sufficient to effect the desired in situ polymerization and to form microdroplets of the oil and resultant polymer.

Thereafter, the discrete, stable microdroplets and polymer are homogeneously distributed throughout the solution. To effect this result, the bulk viscosity of the solution is increased by adding a suitable amount of thickening agent therein to maintain a bulk viscosity from about 10,000 to about 100,000 cps, preferably 20,000 to 60,000 cps.

In general, the thickening agent is present in an amount sufficient to provide product having this predetermined bulk viscosity to maintain the microdroplets in a discrete, stabilized form homogeneously distributed through the medium, without causing deleterious thickening of the product which would make handling difficult. Usually about 0.05–5% by weight of the product is used. The desired amount used will depend, of course, on the particular thickening agent employed. When STABILEZE®(ISP) is used, for example, the preferred amount is about 0.1–1% by weight of the aqueous product, most preferably about 0.4–0.6%.

The presence of the thickener in the product of the invention assures that the discrete, stabilized microdroplets of oil and polymer, for example, silicone oil and polyvinylpyrrolidone will remain homogeneously suspended throughout the product, for an indefinite period of time. Such concentrate may be included in a cosmetic composition, e.g. a shampoo, conditioner, hair spray, mousse, and the like, by using a suitable amount thereof.

Various thickening agents known in the art, and available commercially, may be used in this invention. These include crosslinked methyl vinyl ether-maleic anhydride, sold by International Specialty Products as STABILEZE®, and its hydrolyzed form, or GANTREZ® XL-80W, which can be neutralized upon being added to the aqueous oil-polymer solution.

The thickening agents which are suitable for use herein include: Carbopol®, e.g. Ultrez®, which is a crosslinked polyacrylic acid; carboxymethyl cellulose; Sepigel® 305, which is a polyacrylamide, a $C_{13-14}$ isoparaffin and laureth-7; guar gum; hydroxypropyl guar gum; Lubrajel®, which is a polyglyceryl methacrylate and propylene glycol; xanthan gum, fumed silica, or cellulose ethers such as hydroxyethyl cellulose.

Suitably, the ratio of oil to monomer used in the in situ polymerization and the product obtained thereby should be in the range of about 70–97.5 to 30–2.5, respectively, on a weight percent.

As used herein, a "stable product" means that the discrete oil-polymer microdroplets remain suspended in and homogeneously distributed throughout the aqueous solution for a period of at least seven days at ambient temperature, and, preferably for an indefinite period of time.

The solids content herein is about 5–50%, preferably about 10–30%, by weight of the product.

The viscosity of the stabilized oil in water product, for example, silicone oil, polyvinylpyrrolidone polymer and thickening agent, obtained by in situ polymerization of vinylpyrrolidone monomer, and silicone oil, suitably is thickened in the range of about 10,000 to 100,000 cps, and, preferably, about 20,000 to 60,000 cps.

The diameter of the oil microdroplets obtained are observed to be in the range of about 0.1 to 450 microns, and usually are about 1 to 250 microns.

The invention will now be described with references to the following more particular examples.

EXAMPLE 1

(PVP/Si Weight Ratio 20/80) (20% Solids)

A 1-liter reaction kettle, fitted with a pitched blade Teflon agitator over a flat Teflon blade agitator, was charged with 481 g of water and 112 g of Dimethicone oil (100 or 1000 cs). The oil-in-water mixture was homogenized using a Ross homogenizer which produced a fine microdroplet of the Dimethicone. The reactor was assembled stirring was begun as soon as possible. Concurrently, 28 g of vinyl pyrrolidone (VP) monomer was purged with nitrogen. Then the oil-in-water mixture was heated to 80° C. and the purged VP and 0.05 g of Triganox® 21 was added (time=0). After 30 minutes, 120 minutes and 240 minutes, additional 0.05 g amounts of Triganox® 21 were added. The reaction mixture then was allowed to remain at 80° C. for another 2 hours before the batch was cooled.

After cooling the batch to 70° C., 7.09 g of a 10% NaOH solution was added and the resultant solution was stirred for 10 minutes. Then 70.88 g of GANTREZ XL-80W® (the diacid form of STABILEZE®) was added followed by stirring for 1 hour. Thereafter the neutralized, thickened solution was cooled to 50° C. or below and 0.28 g of benzophenone-4 dissolved in 5 g of water, and 0.07 g of Vitamin E were added. 30 minutes later the resulting product was discharged.

The bulk viscosity, pH, and stability of the reaction product obtained is given in Table I below for various Dimethicone charges.

TABLE I

| Oil | Properties of Invention Product | | |
|---|---|---|---|
| Dimethicone (cps) | Bulk Viscosity (cps) | pH (as is) | Stable |
| 100 | 39,400 | 5.6 | yes |
| 100 | 38,000 | 5.6 | yes |
| 100 | 22,400 | 7.1 | yes |
| 1000 | 54,600 | 4.2 | yes |
| 1000 | 36,400 | 5.9 | yes |
| 1000 | 27,600 | 5.8 | yes |

The microdroplets remained stable and suspended throughout the medium even after aging at 55° C. for 3 months.

EXAMPLE 2

The procedure of Example 1 was followed using 112 grams of a silicone blend of 50/50 100 cs dimethicone and amodimethicone in place of dimethicone oil.

A product with a bulk viscosity from 25,000 to 60,000 cps is obtained.

EXAMPLE 3

The procedure of Example 1 was followed using 112 grams polyphenyl methyl siloxane (Dow Corning 556) in place of dimethicone oil.

A product with a bulk viscosity from 25,000 to 60,000 cps is obtained.

EXAMPLE 4

The procedure of Example i was followed using a silicone blend of 90% cyclomethicone and 10% 100 cs dimethicone in place of dimethicone oil.

A product with a bulk viscosity from 25,000 to 60,000 cps is obtained.

EXAMPLE 5

The procedure of Example 1 was followed using 112 grams of a silicone blend of dimethicone (5 to 100 cs) and a high molecular dimethicone (i.e. a silicone gum or fluid with 1MM to 2.5MM cs viscosity) in place of dimethicone oil.

A product with a bulk viscosity from 25,000 to 60,000 cps is obtained.

EXAMPLE 6

The procedure of Example 1 was followed using 112 grams mineral oil in place of dimethicone oil.

The product had a bulk viscosity of 49,800 cps and its pH was 6.1.

EXAMPLE 7

(PVP/Si Weight Ratio 5/95)

The procedure of Example 1 was followed using 133 grams dimethicone (100 or 1000 cs).

The product had a bulk viscosity of 27,000 cps and its pH was 6.04.

While the invention has been described with particular reference to certain embodiments thereof, it will be understood that changes and modifications may be made which are within the skill of the art. Accordingly, it is intended to be bound only by the following claims, in which:

What is claimed is:

1. An aqueous product consisting essentially of discrete, stabilized microdroplets of an oil and an in situ polymerized water-soluble vinyl monomer, and a thickening agent in an amount of about 0.1–1% by weight to suspend the stabilized microdroplets homogeneously throughout the product at a bulk viscosity of about 25,000 to about 60,000 cps.

2. A product according to claim 1 wherein said monomer is vinyl pyrrolidone.

3. A product according to claim 1 wherein said oil is a cosmetically-active material.

4. A product according to claim 3 wherein said cosmetically-active oil is a silicone, a mineral oil or a water-insoluble organic ester, and blends thereof.

5. A product according to claim 4 wherein said oil is a silicone oil.

6. A product according to claim 5 wherein said silicone oil has a viscosity of about 5 to 600,000 cs.

7. A product according to claim 5 which oil is a blend of high viscosity silicone fluids or silicone gums and low viscosity silicone oils.

8. A product according to claim 1 wherein its solids content is about 5–50% by weight.

9. A product according to claim 8 wherein its solids content is about 10–30% by weight.

10. A product according to claim 1 in which the weight ratio of the oil to polymerized vinyl monomer therein is about 70–97.5 to 30–2.5.

11. A product according to claim 1 wherein said thickener is selected from the group consisting of crosslinked methyl vinyl ether-maleic anhydride copolymer; crosslinked polyacrylic acid; carboxymethyl cellulose; a polyacrylamide, $C_{13-14}$ isoparaffin and laureth-7; guar gum; hydroxypropyl guar gum; a polyglyceryl methacrylate and propylene glycol; xanthan gum, fumed silica, and a cellulose ether.

12. A product according to claim 11 wherein said thickening agent is crosslinked methyl vinyl ether-maleic anhydride copolymer.

13. A process for making the product of claim 1 which comprises providing an aqueous reaction mixture of an oil, a water soluble vinyl monomer and a polymerization initiator, polymerizing said monomer to form discrete, stabilized microdroplets of said oil and said in situ polymerized vinyl monomer, and then adding a thickener to said resulting solution to maintain said microdroplets homogeneously suspended throughout the product.

14. A process according to claim 13 wherein said thickener is a crosslinked methyl vinyl ether-maleic anhydride copolymer which is hydrolyzed and neutralized.

* * * * *